US006837977B1

(12) United States Patent
Dunayevskiy et al.

(10) Patent No.: US 6,837,977 B1
(45) Date of Patent: Jan. 4, 2005

(54) CAPILLARY ELECTROPHORESIS METHOD FOR SCREENING FOR AFFINITY LIGANDS USING A DETECTABLE COMPETITIVE LIGAND

(75) Inventors: Yuriy M. Dunayevskiy, Natick, MA (US); Dallas E. Hughes, Milford, MA (US)

(73) Assignee: Cetek Corporation, Marlborough, MA (US)

(*) Notice: Subject to any disclaimer, the term of this patent is extended or adjusted under 35 U.S.C. 154(b) by 449 days.

(21) Appl. No.: 10/018,233

(22) PCT Filed: Jun. 23, 2000

(86) PCT No.: PCT/US00/17490

§ 371 (c)(1), (2), (4) Date: Dec. 12, 2001

(87) PCT Pub. No.: WO00/79260

PCT Pub. Date: Dec. 28, 2000

Related U.S. Application Data

(60) Provisional application No. 60/140,710, filed on Jun. 24, 1999.

(51) Int. Cl.[7] .............................................. G01N 27/447

(52) U.S. Cl. ....................... 204/451; 204/601; 204/452; 204/453; 204/602; 204/603; 204/604; 204/605; 204/455; 204/606; 204/607; 204/608; 204/610; 204/612; 204/615; 204/616; 204/617; 204/618; 204/621; 436/516; 436/538; 436/540; 436/501; 435/7.1

(58) Field of Search ................................ 204/451, 601, 204/452, 453, 602, 603, 604, 605, 455, 606, 607, 608, 610, 612, 615, 616, 617, 618, 621; 436/516, 538, 540, 501; 435/7.1

(56) References Cited

U.S. PATENT DOCUMENTS

| | | | | |
|---|---|---|---|---|
| 6,299,747 B1 * | 10/2001 | Dunayevskiy et al. | ...... | 204/451 |
| 6,432,651 B1 * | 8/2002 | Hughes et al. | ................. | 435/6 |
| 6,524,866 B1 * | 2/2003 | Hughes et al. | .............. | 436/516 |
| 2002/0052006 A1 * | 5/2002 | Dunayevskiy et al. | ....... | 435/7.1 |

FOREIGN PATENT DOCUMENTS

| | | | |
|---|---|---|---|
| EP | 848251 A2 * | 6/1998 | |
| EP | 0848251 A2 | 6/1998 | ......... G01N/27/447 |
| WO | WO94/09185 | 4/1994 | ............. C25B/7/00 |
| WO | WO96/33412 | 10/1996 | .......... G01N/33/53 |
| WO | WO98/32010 | 7/1998 | ......... G01N/27/447 |
| WO | WO99/18438 | 4/1999 | ......... G01N/33/536 |

* cited by examiner

*Primary Examiner*—Alan Diamond
(74) *Attorney, Agent, or Firm*—Weingarten, Schurgin, Gagnebin & Lebovici LLP

(57) ABSTRACT

The invention relates to a capillary electrophoresis-based method of screening complex materials for any unidentified affinity ligand that binds to a target of interest. The method subjects a plug of a mixture of the target and a complex material sample, and a separate plug of a known, tight-binding competitive ligand, to capillary electrophoresis under conditions optimized to allow mingling of the two plugs during the capillary electrophoresis run. Preferably, migration of the competitive ligand is tracked.

33 Claims, 1 Drawing Sheet

CAPILLARY ELECTROPHORESIS METHOD FOR SCREENING FOR AFFINITY LIGANDS USING A DETECTABLE COMPETITIVE LIGAND

CROSS REFERENCE TO RELATED APPLICATIONS

This application claims priority from U.S. Patent Application No. 60/140,710, filed Jun. 24, 1999, the entirety of which is herein incorporated by reference.

STATEMENT REGARDING FEDERALLY SPONSORED RESEARCH OR DEVELOPMENT

Not applicable.

BACKGROUND OF THE INVENTION

This invention relates to the field of capillary electrophoresis-based screening of materials for unidentified compounds that can bind to a target molecule of interest.

Developing screens to identify new, biologically active compounds can present unique and difficult challenges, especially when screening complex materials, particularly "complex biological materials": any material that may have an effect in a biological system. Examples of complex material include, but are not limited to: naturally occurring complex biological materials, such as natural products or extracts; various biological preparations; chemical mixtures; libraries of pure compounds; and synthetic compounds such as combinatorial libraries. Examples of major screening problems include: detecting candidate hit compounds that bind to a target molecule of interest, especially those present at low concentrations in screened samples; accounting for unknown components that can interfere with screening agents; and determining the relative value of screened samples for further investigative efforts. As well, high concentrations of a weak or several weak, competing binder (s) can mask the signal from a moderate-to-tight-binding affinity ligand occurring at a lower concentration within the same sample.

Therefore, there remains a need for rapid and cost-effective screening tools for discovering new bioactive compounds and potential regulatory compounds, particularly those that bind to essential molecules of key metabolic pathways or molecules implicated in disease. Also needed is a way of prioritizing, for further characterization and testing, samples of material identified to contain potential candidate ligands and/or detected candidate ligands. The present invention addresses these needs, by providing a means of detecting unknown or unindentified ligands that may be candidate, new, bioactive compounds. In particular, the invention provides a means of better identifying ligands having a relative binding strength at or higher than a desired threshold as set by use of a known, preferably detectable, competitive ligand having a selected binding strength or dissociation constant (e.g., $K_d \leqq 100\ \mu M$, preferably $K_d \leqq 10\ \mu M$). Identifying and ranking those ligand-containing samples that form the most stable complexes with the selected target, saves time and resources spent on further isolation and characterization of hit compounds. The most stable ligands are potentially more effective and valuable as therapeutic, regulatory and/or diagnostic compounds and drugs.

BRIEF SUMMARY OF THE INVENTION

The present invention provides a way of identifying new, biologically active compounds when screening various materials, such as naturally occurring complex biological materials, chemical mixtures, synthetic compounds and other materials, for candidate affinity ligands that bind to target molecules of interest (e.g., molecules involved in a disease). Such candidate ligands have potential regulatory, pharmaceutical, therapeutic, and/or diagnostic applications. The methods of the invention combine competitive binding conditions with capillary electrophoresis (CE) to detect, in a screened sample, an unidentified candidate ligand that binds to the target at or above a selected binding strength, and to characterize that candidate ligand's relative binding strength. The method is particularly useful for detecting moderate-to-tight-binding ligands (e.g., with a dissociation constant of preferably about $K_d \leqq 100\ \mu M$, preferably $\leqq 10\ \mu M$ or even $\leqq 10$ nM).

The method involves using a selected target molecule (TG) and a known, preferably moderate-to-tight binding, competitive ligand (CL) that binds to the target (TG), to screen a sample of, e.g., a complex biological material, potentially containing a candidate ligand (LG) that competes with the CL for binding to the TG. Generally, a plug of a mixture of the TG and the sample, and a separate plug of, the CL, are subjected to capillary electrophoresis under conditions optimized to detect the migration of a chosen molecule in unbound state and/or when bound in a complex. Preferably, the detected or tracked molecule is the known, CL, which must be detectable during CE, for instance, by fluorescence or absorbance. By tracking the CL at a detection point in the CE instrument, a capillary electrophoretic migration pattern or profile of the CL is generated. The migration pattern comprises at least one member from the group consisting of a peak representing unbound competitive ligand and a peak representing a complex of the competitive ligand bound to the target. Preferably both peaks are detectable, absent any candidate ligand.

More particularly, the invention encompasses a method of screening a complex material for an unidentified candidate ligand that binds to a pre-selected target of interest (e.g., one implicated in a disease or disorder). The method comprises the following steps:

(a) providing a mixture of the complex material and a predetermined concentration of the target, and separately providing a predetermined concentration of a known, detectable, competitive ligand that binds to the target (preferably a known ligand having a dissociation constant $K_d \leqq 100\ \mu M$, more preferably $K_d \leqq 10\ \mu M$);

(b) sequentially injecting into a capillary of a capillary electrophoresis instrument having a detector (preferably a fluorescence detector), a first plug of analyte and a second plug of analyte, wherein the first and second plugs of analyte comprise a combination selected from the group consisting of:

(i) a combination of the first plug of analyte being of the target/sample mixture and the second plug of analyte being of the competitive ligand; and (ii) a combination of the first plug of analyte being of the competitive ligand and the second plug of analyte being of the target/sample mixture;

(c) subjecting the first and second plugs to capillary electrophoresis under conditions optimized for detecting at least one member selected from the group consisting of unbound competitive ligand and a complex of the competitive ligand bound to the target, and optimized so that detectable analytes from the second plug migrate faster than detectable analyte from the first plug toward the detector and pass through the first plug during capillary electrophoresis, prior to the detectable analytes reaching the detector;

(d) tracking the competitive ligand at the detector to generate a capillary electrophoretic migration pattern; and (e) determining whether a migration pattern resulting from step (d) differs from a reference standard, thereby indicating the presence of a candidate ligand in the complex material.

Other embodiments and details of the invention are set forth below.

DETAILED DESCRIPTION OF THE INVENTION

Figure 1:
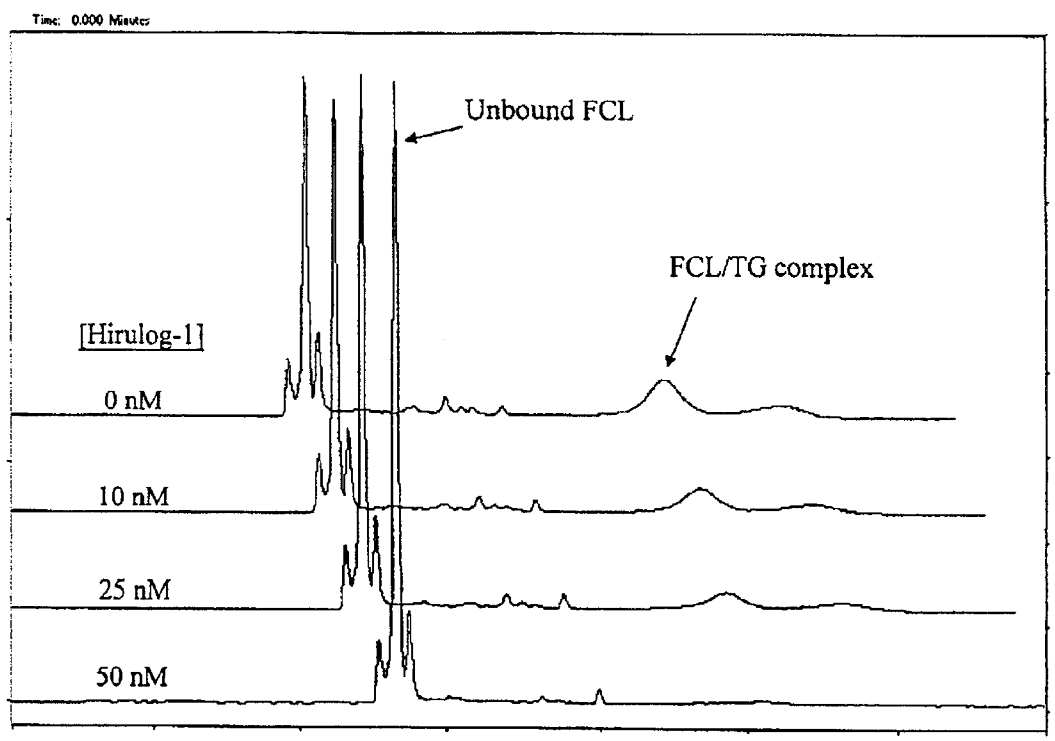
FIG. 1 is an overlay of several electropherograms resulting from using the competitive-binding, CE method of the invention to screen samples containing various concentrations of a test candidate ligand, hirulog-1, which binds tightly to a target molecule, thrombin.

Advantageously, the present invention allows detection of ligands that bind to a selected target, especially moderate-to-tight-binding ones, in mixtures that also contain higher concentrations of competing, weaker-binding ligands. As well, the method does not require knowledge of a candidate ligand's particular structure or concentration within the screened sample in order for it to be detected. The method also enables screening assays using targets that cannot be detected directly during capillary electrophoresis.

In general, the method of the invention works as follows. A predetermined concentration of a target of interest (TG) is first mixed with a sample of complex material to be screened, which may or may not contain one or more potential or candidate ligand(s) (LG) that can bind to the target. The target/sample mixture should be incubated for enough time to allow formation of a complex of the target and any candidate ligand (sometimes referred to as "the TG/LG complex"): e.g., 0.5–30 minutes, preferably 1–5 minutes. Also prepared separately is a predetermined concentration of a known competitive ligand (CL) that is detectable during capillary electrophoresis (e.g., fluorescently labelled CL)—i.e., a compound known to bind to the target, preferably moderately to tightly (e.g., having a dissociation constant $K_d \leqq 100\ \mu M$, preferably about $\leqq 10\ \mu M$). The CL serves to compete with any candidate LG in the screened sample material in binding to target during the capillary electrophoresis (CE) step, described below.

After preparation of the target/sample material mixture and the detectable competitive ligand (CL) solution, a plug of each is injected sequentially into the capillary of a capillary electrophoresis instrument. The order of injection depends on the relative CE migration rates of the CL and the TG under the selected CE conditions. In practicing the method, one uses a capillary electrophoresis (CE) running buffer that will confer a charge on both the CL and the TG. An optional injection of running buffer may be applied between injections to separate the TG/sample and CL plugs. In general, the greater the running buffer plug between the injections, the higher the candidate ligand's a affinity must be in order to be detected. Thus relative affinities of candidate ligands can be determined by repeating the screening protocol with each ligand sample and varying the amount of running buffer injected in between the first and second plugs (i.e., varying the distance traveled by the second plug and hence the time interval before the two plugs mingle).

After injection of the TG/sample and the CL plugs, voltage is applied in an amount appropriate to induce migration of the TG and CL toward and past the detector. For the present screening method to work, it is important that CE conditions are chosen such that detectable analytes from the second-injected plug migrate faster than detectable analytes from the first-injected plug toward a fluorescence detector attached to the CE instrument, during the CE run, so that the detectable analytes from the second plug can migrate through and mingle with detectable analytes from the first plug, prior to the detectable analytes from either of the plugs reaching a detection point in the capillary.

The term "detectable analytes" refers primarily to the competitive ligand (CL) and the target (TG), as well as to any candidate ligand from the sample (LG). The CL is detected directly by the detector, while the TG is detected indirectly when it binds to CL to give a shifted CE migration peak representing the CL/TG complex. Any LG present is indirectly detected via its interruption of CL/TG complex formation, as discussed elsewhere in this disclosure. One of ordinary skill in the art of capillary electrophoresis will appreciate that the detectable analytes from the second-injected plug must have a higher capillary electrophoretic mobility in the direction of the detector, than the detectable analytes from the first plug.

For instance, if a plug of CL analyte is injected, as a second plug, after a first plug containing target (TG) analytes, it is important that unbound CL migrates faster than unbound TG, so that CL analyte molecules from the second-injected plug can move through the TG-containing plug, and CL are thus able to form complex with any free or unbound TG molecules during the CE run. The TG-containing first plug may be a TG/sample plug (as in a screening protocol), or may be a plug of target alone (as when running a control or reference standard).

If the CL plug is injected first, before a second plug containing TG analyte, it is important that the TG analyte has a faster or higher capillary electrophoretic mobility than the CL analyte, so that TG analyte from the second, TG-containing, plug will move through and interact with analyte from the first, CL-containing plug.

Preferably, the known, detectable competitive ligand is tracked at a detector during CE, so that its migration is tracked, thereby generating a capillary electrophoretic migration pattern or profile. The CE migration pattern comprises at least one of the following, if not both: an unbound (free) CL peak and a CL/TG complex peak. For instance, the CL can be fluorescently labeled, allowing monitoring of the CL and/or CL/TG peaks by laser-induced fluorescence detection. Although it is advantageous to use CE conditions allowing observation of both an unbound CL and an bound CL/TG complex during CE, one need observe only one or the other peak in the CE profile for the present screening method to work. Two capillary electrophoretic peaks will be observed in most screenings performed according to the invention: one corresponding to the CL/TG complex and the other corresponding to any unbound CL.

Usually the concentrations of the CL and the TG in their respective plugs are optimized to provide, during CE, a detectable proportion of the CL bound to the TG in the absence of any other target-binding ligand (LG), as discussed further below. One of ordinary skill in the art will readily appreciate what ratio of TG concentration to CL concentration to use, to obtain a desired capillary electrophoretic profile or migration pattern corresponding to a desired amount of the CL complexed to TG in the absence of any other ligand. For instance, in the situation of a target that has a single CL-binding site, and a detectable, tight-binding competitive ligand, one preferably uses equimolar concentrations of each if one wishes to have at least 90–95% of the CL bind to the TG, in the absence of any other ligand.

In general, in order to practice the method of the invention for screening complex material for new affinity ligands, the known, competitive ligand must be detectable during CE and bind to the chosen target stably to form a CL/TG complex, so that the resulting CE migration pattern differs from the CE profile of unbound CL alone. Formation of a CL/TG complex should produce at least an observable decrease in the area of the unbound or free CL peak, and preferably but not necessarily, a separate CL/TG peak. Preferably, but not necessarily, the CL and target concentrations and the CE run time should be used in amounts sufficient to allow the CL plug to mingle with a target-containing plug during CE, by the time either or both of the plugs reach the detection point in the CE instrument. At a minimum, the CL and target concentrations and the time allowed for their interaction during CE should be sufficient to allow enough of the total target and CL available to form a target/CL complex having a detectably different migration peak from that of the unbound CL. In other words, the predetermined target concentration, predetermined competitive ligand concentration, and capillary electrophoresis conditions are pre-selected to produce, absent any other target-binding ligand, a measurable change in the capillary electrophoretic migration pattern generated by the steps of the method. The measurable change comprises a change of at least 10%, preferably at least 50%, advantageously at least 75%, in the peak area of at least one peak selected from the group consisting of a peak representing unbound competitive ligand and a peak representing a complex of the competitive ligand bound to the target. Preferably, a detectable change is seen in both the unbound CL peak area and the bound CL/TG peak area.

If a candidate affinity ligand (LG), particularly a moderate-to-tight-binding LG (e.g., $K_d \leqq 100\ \mu M$, preferably $\leqq 10\ \mu M$) is present in the sample of complex material, the detectable free or unbound CL peak will increase (compared to the migration pattern from a control CE run of TG and CL plugs alone, without any other target-binding ligand). Correspondingly, any detectable CL/TG complex peak will decrease in area, as compared to the migration pattern from the reference or control CE run. This is because the LG remains bound to the TG and does not allow the CL to bind to the TG during the CE run, as the CL plug migrates through the plug of the mixture of TG and LG-containing sample. This results in less CL/TG complex and more unbound CL. Although detection of both peaks is advantageous, only one of the peaks need be observable during CE, preferably the unbound or free CL peak.

The decrease of the CL/TG complex peak, when a screened sample contains a candidate LG, will depend on both the affinity of the LG for the TG and on the LG concentration in the biological sample. Therefore, CE conditions, including the time allowed for interaction between the TG and the CL plugs, can be adjusted to facilitate detection of the presence of a LG that binds to the TG at or above a desired strength or affinity.

The sensitivity of the assay for detecting weak-binding ligands or low concentrations of candidate ligands, may be adjusted by regulating CE conditions to limit the time of interaction between the plug of tight-binding CL and the TG-containing plug, so that at least some portion of any TG/weak-binding LG complex formed may be detected. Decreasing the assay's sensitivity and thus limiting detection to only tight-binding targets, can be achieved by increasing the time before the CL contacts the target (by spacing further apart the TG/sample plug and the CL plug injections, or by selecting appropriate CE conditions in light of the TG's and CE's respective charge-to-mass ratios). Such increased time will give any weak-binding LG/TG complexes more time to dissociate before the TG and CL interact during CE. Target would thus be freed up for binding to the competitive ligand. When tracking CL, this would give rise to a greater CL/TG complex peak and/or decreased unbound CL peak during CE (indicating no tight binder in the screened sample).

By tracking the detectable CL's migration during capillary electrophoresis, the present invention advantageously allows one to screen for candidate ligands to a target that is not itself detectable during capillary electrophoresis. Such undetectable targets may be, for instance, membrane-bound proteins receptors that are not easily purified or are relatively insoluble.

A reference standard for this method comprises the migration pattern of the CL resulting from capillary electrophoresis of sequential injections of a plug of the target without the complex material and a plug of the CL, using the same order of injection and same capillary electrophoresis conditions as in the protocol for screening a sample of complex material.

Methods of detection are known to one of ordinary skill in the art of capillary electrophoresis, and include but are not limited to fluorescence, ultraviolet absorbance, and the like. An advantageous and simple detection means is the use of a fluorescent label on the molecule tracked during CE.

The method of the invention can be used to detect, identify and characterize, both easily and rapidly, moderate-to-tight binding ligands or hit compounds present in samples of complex biological materials (e.g., natural extracts or synthetic compound mixtures). This method is particularly useful to detect, successfully and selectively, low concentrations of tight-binding hit compounds to a selected target of interest, even if the screened sample contains high concentrations of weak-binding candidate ligands or hits.

Before practicing a screening according to the invention, all CE conditions have to be optimized to detect hit ligand(s) with a desired range of affinities, as will be appreciated by one of ordinary skill in capillary electrophoresis. One must define criteria for determining what are a weak-binding hit compound (WB) and a strong-binding affinity ligand. The cut-off for determining the relative binding strength of different ligands or hit compounds is determined primarily by factors such as capillary length, injection-to-detector length, voltage and temperature during CE, buffer composition (e.g., pH and/or salt concentration). For example, tight binders can be found by conducting the CE at higher temperatures (e.g. >25° C.)

The method of the invention is particularly advantageous in identifying, in a screened sample, candidate hit compound (s) having a binding strength higher than a selected threshold, and for determining their relative binding strength. "Moderate-to-strong binding" ligands and "weak-binding" ligands have faster off-rates (Koff) and higher dissociaton constants (KD), and form target/ligand complexes that hold together for little or none of a capillary electrophoretic run, i.e., target/ligand complexes that are unstable and fall apart quickly before coming into contact with CL and before reaching detector. In contrast, stronger or tighter-binding ligands have lower dissociation constants and slower off-rates, forming target/ligand complexes that generally remain bound as they come into contact with CL and migrate past a detector during capillary electrophoresis. Typically, but not always, ligands of a particular binding strength have the respective characteristics shown in Table 1.

TABLE 1

| Ligand's relative affinity for target | Approx. $K_D$ range | Approx. $K_{off}$ range |
|---|---|---|
| Very tight-binding | ≦10 nM | ≦0.01 ($s^{-1}$) |
| Tight-binding | ≦10 $\mu$m | ≦1.0 ($s^{-1}$) |
| Moderate-to-tight-binding | ≦100 $\mu$M | ≦10 ($s^{-1}$) |
| Weak-binding | >100 $\mu$M | >10 ($s^{-1}$) |

Once the capillary electrophroesis conditions are chosen, the screening itself uses the fact that the rate of candidate ligand/target complex dissociation is different between weak ligand/target and strong ligand/target complexes. That is, CE conditions can be optimized to achieve complete or sufficient dissociation of any weak candidate ligand/target complex formed during the pre-CE incubation of sample and target, to free up enough target molecules during the CE for binding to the known competitive ligand, detectably. At the same time, those same optimized CE conditions should allow any moderate-to-tight candidate ligand/target complex that forms during the pre-CE incubation, to remain bound, thus reducing the availability of free target and thereby reducing formation of the TG/CL complex. As a result, the presence of the moderate-to-tight-binding candidate is indicated indirectly, by the change it produces in the CE migration pattern of the known competitive ligand.

One embodiment of the method detects a moderate-to-tight-binding ligand (e.g., having a dissociation constant of about $K_d$≦100 $\mu$M, preferably ≦10 $\mu$M), in preference to a weak-binding ligand (e.g., having a dissociation constant of about $K_d$>100 $\mu$M). The target and a sample of material are first mixed and incubated together to allow binding of the target to any candidate ligand (LG) within the sample. Subsequently, sequential injections of: (1) a plug of the target/sample mixture (containing unbound TG, unbound LG, and any LG/TG complex); and (2) a plug containing CL, are injected into the capillary. The order of the plug injections will be determined by the known, relative CE mobilities of the CL and TG. In some cases, the CL plug is injected first; in other cases, the target/sample plug is injected first. In some cases, a plug of CE running buffer may be injected between the TG/sample and CL plugs.

An exemplary screening according to the invention, in which the CE migration of the competitive ligand is tracked, uses the following steps, with the following results:

1. A plug of a mixture of target and sample complex material, is injected into a capillary electrophoresis instrument. In this example, the TG is negatively charged and has a relatively slow CE mobility.
2. Afterwards, a plug of CL is injected. In this example, the CL is negatively charged and has a higher CE mobility than the TG.
3. Voltage is applied so that migration of the target, whether unbound (TG) or bound to any candidate ligand in the sample (LG/TG complex), and of the CL proceeds towards a detector attached to the CE instrument. The detector may be a fluorescence detector.
4. The CL, because of its higher mobility, begins to catch up to the slower-migrating TG during the CE run.
5. TG that has dissociated from any TG/LG complex during the CE run will be free to bind to CL as the CL plug passes through the TG-containing plug. Any TG remaining bound to LG will not be available to bind to CL.
6. The CL concentrations and CE conditions (including relative time before mingling of the CL and TG/sample plugs) can be set so that, if the LG/TG complex is moderate-to-weak (e.g., having a dissociation constant $K_d$≧100 $\mu$M, preferably ≧10 $\mu$M), most of the weak LG/TG complex will have dissociated before the CL catches up to the TG. The free or unbound TG will bind to the CL and give a large, detectable CL/TG peak, and/or a reduced free or unbound CL peak.
7. If the LG/TG complex is moderate-to-strong (e.g., $K_d$≦1 $\mu$M), the complex will hold together during the CE run and there will be less free TG available to bind to the CL. Thus, the CL/TG peak will be reduced compared to the control without LG present, and the free CL peak will be large.
8. Thus, reduction of the CL/TG complex peak and an increase in the free CL peak indicates the presence of at least one strong-binding candidate ligand (LG) binding to the target, thereby preventing the CL from binding. A higher CL/TG signal and/or a reduced free CL peak will indicate that weak-binding ligand(s) are present.

Exemplary complex materials that can be screened by the present method include, but are not limited to, naturally occurring complex biological materials, chemical mixtures, and synthetic compounds such as combinatorial libraries. Naturally occurring complex biological materials include natural extracts, complex biological material is selected from the group consisting of combinatorial chemical libraries, extracts of terrestrial plants, extracts of marine plants, cells from higher animals including humans, eubacteria, actinomycetes, bacteria, extracts from non-recombinant or recombinant microorganisms, microbial fermentation broths, fungi, protozoa, algae, archaebacteria, worms, insects, marine organisms, sponges, corals, crustaceans, viruses, phages, tissues, organs, blood, soil, sea water, water from a fresh-water body, humus, detritus, manure, mud, and sewage or partially purified fractions thereof. Complex material samples may be diluted and/or fractionated prior to screening by the present methods.

Examples of targets that can be used in the methods of the invention include, but are not limited to, enzymes, receptors, proteins, polypeptides, nucleic acids, polynucleotides, carbohydrates, and chemically, enzymatically, or recombinantly modified forms thereof, the modified forms having been modified for improved electrophoretic properties. The target molecules need not be in purified form, and can be presented as part of, e.g., a cell extract or sonicate, as long as the target itself is accessible for binding to the known competitive ligand. For example, the target may be a G-protein coupled receptor (GPCR) embedded in cell membrane.

Examples of the known, CE-detectable competitive ligand (CL) include, but are not limited to, naturally occurring compounds, synthetic compounds, antibodies, proteins, peptides, oligonucleotides and other drugs known to bind to the target of interest. The competitive ligand may be modified as needed to confer a desired charge to the molecule. Preferably, the CL is moderate-to-tight-binding, with a dissociation constant of about $K_d \leqq 10$ μM and an off-rate of about $K_{off} \leqq 1.0$ ($s^{-1}$) Advantageously, one may use a CL having a $K_d \leqq 10$ nM and a $K_{off} \leqq 0.01$ ($s^{-1}$). A weaker-binding CL may be used (e.g., having a $K_d$ within about 10 μM–100 μM, and an off-rate within about 1.0 ($s^{-1}$) $\leqq K_{off} \leqq 1.0$ ($s^{-1}$)), if used at a higher concentration than used for a moderate-to-tight-binding CL, so as to compensate for the weaker affinity to target.

The methods of the invention use conventional capillary electrophoresis instruments as known in the art. These may use a capillary or a microchip having a plurality of conduits, in each of which CE can be performed. Preferably, the CE capillary has a length within a range of about 0.5–1000 cm, and a diameter within a range of about 10 μm–250 μm. Typical microchip dimensions are in a range of about 0.5–20 cm, and have conduit diameters in a range of about 10 μm–250 μm.

As previously mentioned, a variety of buffer conditions and other factors can be adjusted to achieve a desired sensitivity in the methods of the invention—for instance, to favor detection of tighter-binding candidate ligands having a $K_d \leqq 100$ μM, preferably $K_d \leqq 10$ μM, even more selectively $K_d \leqq 10$ nM. Factors that can be varied include, but are not limited to: capillary length; the distance between the CE starting point and the detector; CE run time; voltage and temperature during CE; and buffer composition, such as its pH and/or salt concentration (i.e., ionic strength). Some examples are given below, but additional modifications will be apparent to one of ordinary skill in the art of capillary electrophoresis, in view of the present disclosure.

Buffer pH values may be within a range of about pH 3–10, preferably pH 5–8. Capillary electrophoresis voltages may be within a range of about 5–30 kV. The salt concentration (e.g., NaCl or KCl) of the CE running buffer can be varied within, e.g., a range of about 0–500 mM, advantageously within 10–100 mM, particularly for proteinaceous targets. Higher salt concentrations (e.g., in a range of about 200 mM–1M) tend to help to stabilize any target/ligand complex. Therefore, using lower salt concentrations favors detection of tighter or stronger binding candidate ligands over weaker-binding ones.

Increasing the CE run time before the TG-sample plug and the CL plug make contact, also favors detection of tighter binding candidate ligands. For instance, a CE run time may be within a range of about 2.5–10.0 minutes. As well, a distance between a capillary electrophoresis start point and the detector may be within a range of about 0.5–1000 cm.

The temperature at which CE is performed can be varied, generally within a range of about 0–60° C., advantageously 5–37° C. Higher temperatures (e.g., about 25–60° C.) can be used to limit the sensitivity of the present screening assay to more tightly binding candidate ligands. Tight-binding ligand/target complexes are generally more stable at higher temperatures, thereby dissociating to a lesser degree than weak ligand/target complexes at the same temperatures.

The present invention can be used in tandem with, or compared against, other capillary electrophoretic methods for screening complex biological materials, such as those found in Hughes et al., U.S. Pat. No. 5,783,397, wholly incorporated herein by reference.

Additionally, the present methods can be used to determine the relative binding strength or affinity of a candidate ligand in a screened sample, if the concentration of the candidate ligand is known. The relative affinity can be determined by varying, over several CE runs, the amount of time before the CL plug contacts and mingles with the TG/sample plug, and observing, measuring, and comparing the relative areas of the observed CE peaks (representing unbound CL and TG/CL complex) in each run.

Moreover, one of ordinary skill in the art will appreciate that the present screening method can be coupled with fractionation, purification, and/or analytical techniques (such as liquid chromatography or mass spectrometry), as known in the art, in order to isolate and to characterize a candidate ligand detected in a complex material sample by the screening method.

EXAMPLES

Figure 2:
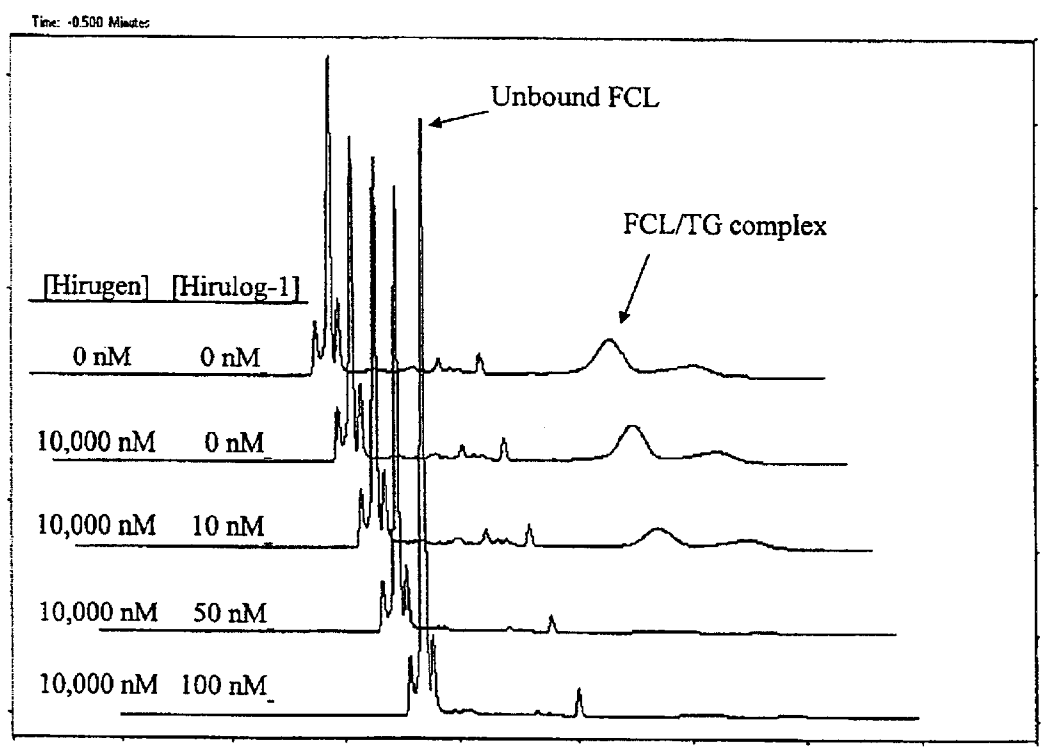
FIG. 2 is an overlay of several electropherograms resulting from using the competitive-binding, CE method of the invention to screen several samples each containing two test candidate thrombin-binding ligands, weak-binding hirugen and tight-binding hirulog-1, at various concentrations.

The invention is further described by way of the following, non-limiting examples, the CE results of which are illustrated in FIGS. 1 and 2. Both FIGS. 1 and 2 show overlays of several electropherograms from screening several samples according to the method of the invention, with each sample having a different concentration of a candidate ligand. The X-axis represents the time elapsed from the start of the CE run, and the Y-axis represents the relative fluorescence signal (i.e., amount) of the CL detected by the detector of the CE instrument.) However, the X-axis and Y-axis are offset for each electropherogram, in order to visualize the height differences in the unbound CL peak and CL/TG complex peak observed under the various conditions.

Example 1

FIG. 1 demonstrates an experiment where 50 nM of a target, the anticoagulant protein, thrombin (TG), is first incubated, prior to CE, for 5 minutes with different concentrations of a test candidate ligand: the tight-binding synthetic ligand, hirulog-1 (D-Phe-Pro-Arg-Pro-$(Gly)_4$-Asn-Gly-Asp-Phe-Glu-Glu-Ile-Pro-Glu-Glu-Tyr-Leu; $K_d \sim 2 \times 10^{-9}$M). Also prepared is 100 nM of a fluorescently labeled, tight-binding competitive ligand, single-stranded (ss) DNA oligonucleotide 5'-fluorescein-GGTTGGTGTGGTTGG-3' ($K_d = 3 \times 10^{-9}$ M; hereinafter "FCL"). The mixture of target and candidate ligand (TG/LG) is first injected into the CE instrument for about ten (10) seconds to give a first plug, followed by a 10-second injection of FCL as the second plug.

Voltage of about 20 kV is applied to initiate electrophoresis, and the unbound competitive ligand (FCL) and bound FCL/TG complex peaks are monitored during CE by means of laser-induced fluorescence and a fluorescence detector positioned at a detection point along the capillary.

Referring to the electropherograms shown in FIG. 1, with no hirolog-1 present in the target/sample mixture, a large FCL/TG complex peak is observed in addition to an unbound (free) FCL peak. At increasing concentrations of the test candidate ligand, hirulog-1, the FCL/TG complex peak becomes reduced and the amount of unbound FCL increases. This is because the hirulog-1 binds to the FCL-binding site of the target during the pre-CE incubation and stays bound during the CE run, reducing the amount of unbound TG available to bind FCL when the FCL plug reaches and interacts with the plug of TG/sample mixture. With 50 nM hirulog-1 in the sample, equivalent to the concentration of TG, virtually all the TG is bound to hirulog-1, resulting in a complete disappearance of the FCL/TG complex peak and the appearance of just the unbound FCL peak.

Example 2

FIG. 2 demonstrates an experiment where a tight-binding, test candidate ligand, hirulog-1, is detected even in the presence of high concentrations of a weak-binding test candidate ligand, hirugen (Gly-54-Leu-65 carboxyterminal dodecapeptide of hirudin with sulfated tyrosine; $K_d$=1.5×$10^{-7}$ M). Here the thrombin target (TG) is incubated, prior to CE, for five minutes with samples containing hirugen and hirulog-1 at different concentrations. Each of these target/sample mixtures is subjected to a CE screening run, as follows. A plug of target/sample mixture is pressure-injected into the CE instrument for 10 seconds to give a first-injected plug. A second injection plug of 100 nM FCL is then injected for 10 seconds, and then voltage of about 20 kV is applied to start electrophoresis. The CE migration of the FCL and FCL/TG complex are monitored by way of laser-induced fluorescence. Again, the FCL has a higher electrophoretic mobility than the TG, so that the unbound FCL peak appears before that of the FCL/TG complex (see FIG. 2).

With no hirugen or hirulog-1 present, the fast-migrating FCL migrates through the slower-migrating TG during the CE run, and the FCL/TG complex is formed as the FCL passes through the TG. This results in a similar electrophoretic profile (top-most trace in FIG. 2) that is similar to FIG. 1, top-most electropherogram: i.e., both an unbound FCL peak and an FCL/TG peak are observed.

Pre-incubation of the thrombin target with 10,000 nM hirugen, prior to CE, produces no difference in the competitive ligand's (FCL's) CE profile. This is because the hirugen is weak enough that most, or all, of the hirugen/TG complex formed during the pre-capillary incubation period, dissociates during the CE run before the FCL 'catches up' and contacts the TG. In other words, under these conditions, the method is insensitive to the relatively weak-binding ligand, hirugen.

However, the method detects the tight-binding candidate ligand, hirulog. The hirulog-1/TG complex is sufficiently strong to remain together during the CE run until the FCL catches up to the target. Due to the stability of the hirulog-1/TG complex, there is less TG available to bind to the FCL. This results in a decrease in the FCL/TG peak. As seen in the electropherograms, the hirulog-1 signal is detectable even in the presence of up to 1,000-fold molar excess of the weak-binding hirugen.

As demonstrated, the invention thus provides a method for determining which screened samples contain low concentrations of tight-binding compounds in the presence of high concentrations of weak-binding compounds. This method is advantageous for screening complex mixtures such as natural extracts, which often contain such a mix of candidate ligands. By adjusting the conditions, repeating the screening method under different CE conditions, and comparing the resulting electropherograms, one may also be able to estimate the relative affinity of the ligands present for the target. Some conditions that may be varied include, but are not limited to, sample concentration or dilution amount, buffer pH and/or salt concentration, CE voltage, capillary temperature, and the interval of time or distance between the first and second plugs.

While the present invention has been described in conjunction with exemplary embodiments, one of ordinary skill, after reading the foregoing specification, will be able to effect various modifications or to substitute equivalents in practicing the methods set forth herein, without departing from the spirit of the invention as defined by the claims. It is therefore intended that the invention protection granted by any patent issuing from this application be limited by only the appended claims and equivalents thereof.

What is claimed is:

1. A method of screening a complex material for an unidentified candidate ligand that binds to a pre-selected target, comprising the steps of:

(a) providing a mixture of the complex material and a predetermined concentration of the target, resulting in a target/sample mixture, and separately providing a predetermined concentration of a known, detectable, competitive ligand that binds to the target;

(b) sequentially injecting into a capillary of a capillary electrophoresis instrument having a detector, a first plug of analyte and a second plug of analyte, wherein the first and second plugs of analyte comprise a combination selected from the group consisting of:

(i) a combination of the first plug of analyte being of the target/sample mixture and the second plug of analyte being of the competitive ligand; and (ii) a combination of the first plug of analyte being of the competitive ligand and the second plug of analyte being of the target/sample mixture;

(c) subjecting the first and second plugs to capillary electrophoresis under conditions optimized for detecting at least one member selected from the group consisting of unbound competitive ligand and a complex of the competitive ligand bound to the target, and optimized so that detected analytes from the second plug migrate faster than detected analytes from the first plug toward the detector and pass through the first plug during capillary electrophoresis, prior to the detected analytes reaching the detector;

(d) tracking the competitive ligand at the detector to generate a capillary electrophoretic migration pattern; and (e) determining whether the migration pattern from step (d) differs from a reference standard, thereby indicating the presence of a candidate ligand in the complex material.

2. The method of claim 1, wherein the reference standard comprises a reference migration pattern resulting from: (a) capillary electrophoresis of sequential injections of a plug of the predetermined concentration of target without the complex material and a plug of the competitive ligand, using a same order of injection and same capillary electrophoresis conditions as used in claim 1; and (b) tracking the competitive ligand at the detector.

3. The method of claim 1, wherein the first plug is of the target/sample mixture and the second plug is of the competitive ligand.

4. The method of claim 3, wherein the competitive ligand has a higher capillary electrophoretic mobility than the target in a direction of the detector.

5. The method of claim 1, wherein the first plug is of the competitive ligand and the second plug is of the target/sample mixture.

6. The method of claim 5, wherein the target has a higher capillary electrophoretic mobility than the competitive ligand in a direction of the detector.

7. The method of claim 1, 2, 3, or 5, wherein the migration pattern comprises at least one member from the group consisting of a peak representing unbound competitive ligand and a peak representing a complex of the competitive ligand bound to the target.

8. The method of claim 1, 3, or 5, wherein the target comprises a member selected from the group consisting of enzymes, receptors, proteins, polypeptides, nucleic acids, polynucleotides, carbohydrates, and chemically, enzymatically, or recombinantly modified forms thereof, wherein the modified forms have been modified for improved electrophoretic properties.

9. The method of claim 1, 3, or 5, wherein the complex material is selected from the group consisting of combinatorial chemical libraries, extracts of terrestrial plants, extracts of marine plants, cells from higher animals including humans, eubacteria, actinomycetes, bacteria, extracts from non-recombinant or recombinant microorganisms, microbial fermentation broths, fungi, protozoa, algae, archaebacteria, worms, insects, marine organisms, sponges, corals, crustaceans, viruses, phages, tissues, organs, blood, soil, sea water, water from a fresh-water body, humus, detritus, manure, mud sewage and partially purified fractions thereof.

10. The method of claim 1, 3, or 5, wherein the known, competitive ligand is a member selected from the group consisting of naturally occurring compounds, synthetic compounds, antibodies, proteins, peptides, and oligonucleotides known to bind to the target.

11. The method of claim 1, 3, or 5, wherein the known, competitive ligand is detectable by a fluorescence detector.

12. The method of claim 1, 3, or 5, wherein the competitive ligand has a dissociation constant ($K_d$) within a range of about 10 $\mu$M–100 $\mu$M and an off-rate ($K_{off}$) of about 1.0 $(s^{-1}) \leqq K_{off} \leqq 10\ (S^{-1})$.

13. The method of claim 12, wherein the predetermined concentration of the competitive ligand is at least about 5.0 $\mu$M.

14. The method of claim 1, 3, or 5, wherein the known competitive ligand has a dissociation constant $K_d$ within a range of about 10 nM–10 $\mu$M and an off-rate ($K_{off}$) within a range of about 0.01 $(s^{-1})$–1.0 $(s^{-1})$.

15. The method of claim 1, 3, or 5, wherein the known competitive ligand has a dissociation constant of about $K_d$<10 nM and an off-rate of about $K_{off}$<0.01 $(s^{-1})$.

16. The method of claim 1, 3, or 5, wherein the predetermined target concentration, predetermined competitive ligand concetration, and capillary electrophoresis conditions are pre-selected to produce, absent any other target-binding ligand, a measurable change in the capillary electrophoretic migration pattern.

17. The method of claim 16, wherein the measurable change comprises a change of at least 10% in peak area of at least one peak selected from the group consisting of a peak representing unbound competitive ligand and a peak representing a complex of the competitive ligand bound to the target.

18. The method of claim 16, wherein the measurable change comprises a change of at least 50% in peak area of at least one peak selected from the group consisting of a peak representing unbound competitive ligand and a peak representing a complex of the competitive ligand bound to the target.

19. The method of claim 16, wherein the measurable change comprises a change of at least 75% in peak area of at least one peak selected from the group consisting of a peak representing unbound competitive ligand and a peak representing a complex of the competitive ligand bound to the target.

20. The method of claim 16, wherein the measurable change comprises a change of at least 10% in peak area of a peak representing unbound competitive ligand and a change of at least 10% in peak area of a peak representing a complex of the competitive ligand bound to the target.

21. The method of claim 1, 3, or 5, wherein capillary electrophoresis conditions are optimized to allow detection of a candidate ligand having a dissociation constant ($K_d$) within a range of about 10 $\mu$M–100 $\mu$M and an off-rate ($K_{off}$) within a range of about 0.01 $(s^{-1})$–1.0 $(s^{-1})$.

22. The method of claim 1, 3, or 5, wherein capillary electrophoresis conditions are optimized to allow detection of a candidate ligand having a dissociation constant ($K_d$) within a range of about 10 nM–10 $\mu$M and an off-rate ($K_{off}$) within a range of about 0.01 $(s^{-1})$–1.0 $(s^{-1})$.

23. The method of claim 1, 3, or 5, wherein capillary electrophoresis conditions are optimized to allow detection of a candidate ligand having a dissociation constant of about $K_d \leqq 10$ nM and an off-rate of about $K_{off} \leqq 0.01\ (s^{-1})$.

24. The method of claim 1, 3, or 5, further comprising injecting between the first plug and second plug, a plug of capillary electrophoresis running buffer.

25. The method of claim 1, 3, or 5, wherein capillary electrophoresis is performed using a running buffer having a pH value within a range of about pH3–pH10.

26. The method of claim 1, 3, or 5, wherein capillary electrophoresis is performed using a running buffer having a pH value within a range of about pH5–pH8.

27. The method of claim 1, 3, or 5, in which capillary electrophoresis is performed using a running buffer having a salt concentration within a range of about 0–500 mM.

28. The method of claim 1, 3, or 5, in which capillary electrophoresis is performed at a temperature within a range of about 0–60° C.

29. The method of claim 1, 3, or 5, in which capillary electrophoresis is performed at a temperature within a range of about 5–37° C.

30. The method of claim 1, 3, or 5, in which capillary electrophoresis is performed with a run time within a range of about 0.5–60 minutes.

31. The method of claim 1, 3, or 5, in which a distance between a capillary electrophoresis start point and the detector is within a range of about 0.5–1000 cm.

32. The method of claim 1, 3, or 5, in which capillary electrophoresis is performed in a capillary having a length within a range of about 0.5–1000 cm.

33. The method of claim 1, 3, or 5, in which capillary electrophoresis is performed in a conduit of a microchip.

* * * * *